United States Patent [19]

Desmurs et al.

[11] Patent Number: 5,189,220
[45] Date of Patent: Feb. 23, 1993

[54] PROCESS FOR PREPARING N-ALKYLANILINES AND N-ALLYLANILINES CATALYZED BY IODIDES

[75] Inventors: Jean Desmurs, Communay; Jean-Pierre Lecouve, Caluire, both of France

[73] Assignee: Rhone-Poulenc Chimie, Cedex, France

[21] Appl. No.: 674,316

[22] Filed: Mar. 25, 1991

Related U.S. Application Data

[63] Continuation of Ser. No. 386,112, Jul. 28, 1989, abandoned.

[30] Foreign Application Priority Data

Jul. 29, 1988 [FR] France ................................ 88 10249

[51] Int. Cl.$^5$ ............................................ C07C 209/10
[52] U.S. Cl. ...................................... 564/404; 564/405
[58] Field of Search ............... 564/404, 405, 440, 441, 564/442

[56] References Cited

U.S. PATENT DOCUMENTS

| | | | |
|---|---|---|---|
| 2,286,678 | 6/1942 | Gubelmann | 564/404 |
| 3,668,254 | 6/1972 | D'Amico et al. | 564/434 |
| 3,819,708 | 6/1974 | Manning | 564/443 |
| 4,126,689 | 11/1978 | Sanczuk et al. | 514/329 |
| 4,701,560 | 10/1987 | Regimbeau et al. | 564/404 |
| 4,956,496 | 9/1990 | Denis et al. | 564/404 |

FOREIGN PATENT DOCUMENTS

| | | | |
|---|---|---|---|
| 0019158 | 11/1980 | European Pat. Off. | 564/442 |
| 0205391 | 12/1986 | European Pat. Off. | 564/404 |
| 2305434 | 3/1976 | France . | |
| 1336484 | 4/1988 | U.S.S.R. | 564/404 |

*Primary Examiner*—Carolyn Elmore
*Assistant Examiner*—Brian M. Burn
*Attorney, Agent, or Firm*—Finnegan, Henderson, Farabow, Garrett and Dunner

[57] ABSTRACT

The present invention relates to a process for the N-alkylation and N-allylation of an aniline by bringing the aniline into contact with an alkylating or allylating agent in an organic solvent in a homogenous liquid phase in the presence of an iodide and a stoichiometric amount of non-quaternizable base.

18 Claims, No Drawings

PROCESS FOR PREPARING N-ALKYLANILINES AND N-ALLYLANILINES CATALYZED BY IODIDES

This application is a continuation of application Ser. No. 07/386,112 filed Jul. 28, 1989, now abandoned.

BACKGROUND OF THE INVENTION

The present invention relates to a process for preparing N-alkylanilines and N-allylanilines. It relates more specifically to the preparation of N-allylanilines, and still more specifically to the preparation of N-monoallylanilines.

The preparation of N-monoallyanilines is especially important. For example, in the case of trifluoromethylaniline, the monoallyl derivative obtained is an important intermediate in the synthesis of a herbicide as described in French Patent 2,305,434. According to this patent, to prepare the desired herbicide, 3-[N-(meta-trifluoromethylphenyl)]-3-chloro-4-chloromethyl-2-pyrrolidone, it is necessary to start with a trifluoromethylaniline and protect one of the hydrogen atoms by adding an acetyl group before performing the allylation to create a monofluoromethylaniline. The object of these extra steps is to avoid the formation of diallyl by-products which are unusable.

There has been a long felt need in the industry to find a means of preparing a monoallyltrifluoromethylaniline directly in a single stage, instead of the three stages as described in French Patent 2,305,434, with good yields calculated with respect to the starting material employed, meta-trifluoromethylaniline, which is a very expensive compound which the industry has no wish to waste.

U.S. Pat. No. 4,701,560 attempted to solve this problem with a process for the allylation of meta-trifluoromethylaniline in a two-phase, water/organic solvent medium in the presence of an inorganic base chosen from carbonates or sodium hydroxide and the presence of catalytic amounts of a quaternizable tertiary amine. To reduce the amount of undesirable diallyl by-products, it is necessary to limit the degree of conversion of the meta-trifluoromethylaniline, and hence to work in the presence of a deficiency of allyl halide; it is specified in this text that the ratio of meta-trifluoromethylaniline to the allyl halide is preferably approximately 2:1. Thus, the starting material is used in a non-stoichiometric amount and the yields of N-monoallyltrifluoromethylaniline calculated with respect to the meta-trifluoromethylaniline introduced do not exceed 40%. This is insufficient for an economically profitable and commercially successful process.

Allylation reactions with anilines other than metatrifluoromethylaniline are also described. For example, U.S. Pat. No. 2,286,678, describes the allylation of para-hydroxyaniline in a medium consisting of an alcohol and in the presence of carbonate as a neutralizing agent.

The stated yields of N-monallylhydroxyaniline do not exceed those of the previous patent. Also, this process results in the formation of a significant amount of diallyl derivatives which are undesirable byproducts. Therefore, this technique is also not applicable to the preparation of a N-monoallylated product in a single stage with good yield and little production of unwanted diallyl derivatives.

A process which consists of allylating 4-aminodiphenylamine with 2,3-dichloropropene in the presence of triethylamine is described in U.S. Pat. No. 3,668,254. The stated yields, as in the previous two processes, do not exceed 40%. In addition, triethylamine is used in a more than stoichiometric amount relative to the allyl halide. From an economic standpoint, this technique is disadvantageous on two accounts: the yields are low and the cost of the starting materials employed is too high.

U.S. Pat. No. 3,819,708 describes the alkylation of para-phenylenediamines in various solvents, in the presence of a tertiary amine such as triethylamine or of an inorganic base as neutralizing agent for the hydracid formed. The alkylating agents which are described are much less reactive than allyl halides, and the problem of dialkylation is hence much smaller. The selectivity, that is to say the yield of monoalkyl product relative to the dialkyl derivatives, is never described.

Despite the existence of abundant literature describing the alkylation or allylation of various anilines, no process has ever been developed which solves the problems of preparing a N-monoalkylaniline or N-monoallylaniline using a process that produces a good yield of the monosubstituted compared to the disubstituted N-aniline.

It is the object of the present invention to provide a new process for producing N-alkylation and N-allylation of an aniline which avoids the disadvantage of the previously known processes. The new process will enable someone skilled in the art to produce high yields of N-monoalkylated or N-monoallylated anilines with very low formation of unusable dialkyl or diallyl derivatives.

Additional objects and advantages of the invention will be set forth in the description which follows, and in part will be apparent from the description, or may be learned by practice of the invention. The objects and advantages of the invention may be realized and obtained by means of instrumentalities and combinations particularly pointed out in the appended claims.

SUMMARY OF THE INVENTION

To achieve the foregoing objects, and in accordance with the purposes of the invention as embodied and broadly described herein, there is provided a process for the N-alkylation and N-allylation of an aniline, wherein the aniline and an alkylating or allylating agent are brought into contact in an organic solvent in a homogenous liquid phase in the presence of an iodide and a stoichiometric amount of a non-quaternizable base.

The alkylating or allylating agent is chosen from alkyl halides or sulfates in which the alkyl chain can contain unsaturated bonds, can be linear or branched and can, in addition, contain substituents chosen from halo, aryl, aralkyl, haloaryl and nitroaryl radicals.

Among halides, it is preferable to use chlorides and bromides, and most especially chlorides because they are less expensive.

Among alkyl or allyl halides, the present invention relates more specifically to allyl halides, since they are agents of low reactivity with respect to alkylation, especially the chlorides.

Some of the alkylating or allylating agents which may be used are:
allyl iodide
allyl chloride
allyl bromide
benzyl chloride
benzyl bromide isopropyl bromide
crotyl chloride 1-chloro-2-butene The process of the present invention may be applied to any anilines. Anilines of low basicity having a pKa of less than 4.5 are particularly preferred.

The preferred anilines, those possessing a pKa of less than 4.5, are represented by the following formula (I):

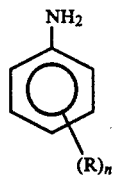

in which
R denotes:
a halogen
a group $-AC_nX_{2n+1}$ where X denotes halogen, A denotes a covalent bond,
or an oxygen or sulfur atom,
a nitro group.
n is equal to 0, 1 or 2.

Some of the preferred anilines of formula (I), which may be used are:
aniline
chloroanilines
fluoroanilines
nitroanilines
trihalomethylanilines
trihalomethoxyanilines
trihalomethylthioanilines The iodides which may be used within the framework of the present invention are chosen from the onium iodides, the alkali metal iodides or allyl iodide.

The onium ions referred to in the present invention are cations where the covalency of a specific element in an uncharged compound is increased by coordination with hydrocarbon residues. The resultant ion is called an "onium ion."

The onium ions used in the process according to the invention are those derived, in particular, from nitrogen, phosphorus, arsenic, sulfur, selenium, oxygen, carbon or iodine. The onium ions derived from nitrogen, phosphorus or arsenic will be tetracoordinated, the onium ions derived from sulfur, selenium, oxygen, carbon or S=O will be tricoordinated.

The hydrocarbon reissues coordinated to these different components are alkyl, alkenyl, aryl, cycloalkyl or arylalkyl radicals, optionally substituted, it being possible for two coordinated hydrocarbon residues to form together a single divalent Some examples of onium ions which may be used include:
Alkylammoniums and arylammoniums such as:
tetraethylammonium,
tetrabutylammonium,
dodecyltrimethylammonium,
tetrapropylammonium,
tetrapentylammonium,
tetrahexylammonium,
tetraheptylammonium,
tetraoctylammonium,
tetradecylammonium,
benzyltrimethylammonium,
benzyltributylammonium,
benzyltriethylammonium,
phenyltrimethylammonium,
methyltriphenylammonium,
Alkylphosphoniums such as:
tetramethylphosphonium,
tetrabutylphosphonium,
trimethylphenylphosphonium,
methyltri(isopropyl)phosphonium,
methyltriphenylphosphonium,
methyltribenzylphosphonium,
tetraethylphosphonium,
tetraphenylphosphonium,
tetraphenylarsonium.
The sulfoniums such as:
trimethylsulfonium,
triethylsulfonium,
triphenylsulfonium,
various onium ions such as:
trimethylsulfoxonium,
triphenylcarbenium,
triethyloxonium.

In the class of onium ions, it is preferable to use onium ions which have a molecular weight of between 150 and 400, and more preferably between 200 and 300. Among these onium ions, ammonium ions in which the four alkyl groups are similar and possess four to five carbon atoms are especially preferred.

The onium compound can be soluble in the reaction medium, in which case the reaction will take place in a homogenous medium, or insoluble in solid form, in which case reaction will take place in a two-phase, solid/liquid medium.

The onium compound can also be supported on an inorganic or polymeric resin.

Examples of "supported" onium compounds, are:
tetrabutylammonium fluoride on silica gel
tributylammonium chloride on polymer marketed, for example, by the FLUKA company
methyltributylphosphonium chloride linked to polystyrene marketed, for example, by the FLUKA company.

When the onium compound is supported on an inorganic or polymer resin, the reaction will take place in a two-phase, solid/liquid medium.

The alkali metal iodides which may be used include sodium or potassium iodide. These iodides may be used as such or in the presence of a complexing agent.

The complexing agents may be chosen from the macrocyclic polyethers known under the general name of "crown ethers" which are described in U.S. Pat. No. 3,562,295; they may also be chosen from the tertiary amines containing three polyalkyleneoxy groups which are described in U.S. Pat. No. 4,343,745. Some of the amines which may be used are:
tris(3,6-dioxaheptyl)amine
tris(3,6,9-trioxadecyl)amine
tris(3,6-dioxaoctyl)amine
tris(3,6,9-trioxaundecyl)amine
tris(3,6-dioxanonyl)amine
tris(3,6,9-trioxadodecyl)amine The base used in the process of the invention serves to neutralize the hydracid liberated during the alkylation. It may be chosen from inorganic bases such as sodium hydroxide or carbonates, or from organic bases such as sodium acetate, or non-quaternizable tertiary amines.

Non-quaternizable tertiary amines are understood to mean all tertiary amines possessing at least one branched alkyl chain, and preferably at least two branched alkyl chains. Examples of such amines, are:
   diisopropylallylamine
   diisopropylethylamine
   triisopropylamine.

Among the group of bases mentioned, it is preferable to use diisopropylethylamine.

The solvent forming the reaction medium must solubilize the aniline and the alkyl or allyl halide; the onium compound or the base, which can be solid, are not always solubilized by the reaction medium, but it is nevertheless preferable that they are both soluble in the reaction medium.

The solvents are chosen from:
   Aliphatic hydrocarbons such as
   hexane
   cyclohexane
   heptane
   octane
   Aromatic hydrocarbons such as
   toluene
   xylene
   Halogenated hydrocarbons such as
   chloroform
   methylene chloride
   chlorobenzene
   carbon tetrachloride
   dichloroethane
   Alcohols such as
   ethanol
   isopropanol
   butanol
   octanol
   Polar aprotic solvents such as
   N,N-dimethylformamide
   acetonitrile
   N-methylpyrrolidone
   Non-quaternizable tertiary amines such as
   diisopropylethylamine.

Among the group of solvents mentioned, it is preferable to use heptane or diisopropylethylamine.

For improved implementation of the invention, it is preferable to use an approximately stoichiometric amount of alkyl or allyl halide relative to the aniline.

The onium compound is used in a catalytic amount, which is a molar ratio of between 0.025 and 0.2 relative to the aniline.

The preferred reaction temperature is between 0° and 150° C. The temperature will vary according to the reactants brought into contact, especially according to the pKa of the aniline and the nature of the halide.

The reaction pressure is preferably atmospheric pressure.

The reaction time varies between one and a few hours.

These and other features and advantages of the present invention will be more apparent from the following description of the preferred embodiments which are not to be regarded as limiting the invention.

EXAMPLES 1 AND 2

INFLUENCE OF AMMONIUM IODIDES

A 30 ml reactor is charged with:
0.64 g of m-trifluoromethylaniline (4 mmol)
0.3 g of allyl chloride (4 mmol)
2 ml of solvent
0.51 g of diisopropylethylamine (4 mmol) and, where appropriate, 0.4 mmol of an ammonium iodide. The reaction mixture is heated for 3 h 30 min at 80°. At the end of the reaction, after cooling, 5 ml of N sodium hydroxide are added. The organic products are extracted with 3×10 ml of isopropyl ether.

The combined organic phase is diluted to 50 ml in a volumetric flask for assay by GC.

In the following tables, the degree of conversion (DC) is calculated as follows:

TABLE 1

$$DC = \frac{\text{number of moles of aniline converted}}{\text{number of moles of aniline introduced}} \%$$

$$YD = \frac{\text{number of moles of product formed}}{\text{number of moles of aniline converted}} \%$$

$$\text{Selectivity} = \frac{\text{amount of N-alkyl or N-allyl formed}}{\text{amount of N-alkyl of N-allyl formed} + \text{amount of dialkyl or diallyl formed}} \%$$

| Exp. | Ammonium | DC mTFMA | YD N-allyl | YD N,N-di-allyl | Accounted for | Selectivity |
|---|---|---|---|---|---|---|
| C1 | — | 7.5% | 100% | 0% | 100% | |
| 1 | +NET4I− | 72.5% | 93.1% | 6.8% | 100% | 93.1% |
| 2 | +NBu4I− | 73.7% | 88.1% | 8.5% | 97.5% | 91.2% |

EXAMPLES 3 AND 4

INFLUENCE OF THE NATURE OF THE ONIUM ION

The procedure is as in Example 1, charging:
0.64 of m-trifluoromethylaniline (4 mmol)
0.3 of allyl chloride (4 mmol)
0.51 g of diisopropylallylamine (4 mmol)
2 ml of heptane
and 0.4 mmol of an onium iodide. The reaction is carried out at 80° for four hours.

TABLE 2

| Exp. | Onium | DC mTFMA | YD N-allyl | YD diallyl |
|---|---|---|---|---|
| 3 | (Me)$_3$SI=O | 18.4% | 83.3% | trace |
| 4 | (Me)$_3$SI | 54.5% | 91.4% | 5.9% |

EXAMPLES 5 TO 10

INFLUENCE OF ALKALI METAL IODIDES OR COMPLEX ALKALI METAL IODIDES

The procedure is as in Example 1, charging:
0.64 g of m-trifluoromethylaniline (4 mmol)
0.3 g of allyl chloride (4 mmol)
2 ml of heptane
0.51 g of diisopropylethylamine (4 mmol)
4 mmol of an alkali metal iodide
and, where appropriate, 0.4 mmol of a complexing agent (TDA1 indicates tridioxaheptylamine).

TABLE 3

| Exp. | Salt | Complexing agent | DC mTFMA | YD N-allyl | YD diallyl |
|---|---|---|---|---|---|
| C2 | NaCl | | 0% | | |
| C3 | NaBr | | 1% | | |
| 5 | NaI | | 75.7% | 88% | 6.4% |
| 6 | NaI | 15crown5 | 93.2% | 81.7% | 14.5% |
| 7 | NaI | TDA-1 | 66% | 83% | 7.5% |
| 8 | KI | | 58% | 95.8% | 4.6% |
| 9 | KI | 18crown6 | 66% | 91.6% | 6.8% |

TABLE 3-continued

| Exp. | Salt | Complexing agent | DC mTFMA | YD N-allyl | YD diallyl |
|---|---|---|---|---|---|
| 10 | KI | TDA-1 | 74% | 78.6% | 6.7% |

EXAMPLES 11 TO 25

INFLUENCE OF REACTION TIME

The procedure is as in Example 1, charging:
1.28 g of m-trifluoromethylaniline (8 mmol)
0.6 g of allyl chloride (8 mmol)
4 ml of heptane
1.02 g of diisopropylethylamine (8 mmol)
0.8 mmol of sodium iodide.
The reactions are carried out at different temperatures.

TABLE 4

The results reported in Table 4 were obtained at 70° C.

| Exp. | Time in min | DC mTFMA | YD N-allyl | YD di-allyl | Ac-counted for | Selectivity mono mono + di |
|---|---|---|---|---|---|---|
| 11 | 240 | 72.2% | 83% | 13.2% | 97.2% | 86.2% |
| 12 | 120 | 58.4% | 79.8% | 11.4% | 94% | 87.5% |
| 13 | 60 | 55% | 95.3% | 8% | 102% | 92% |
| 14 | 30 | 14% | 54.5% | traces | 83% | 100% |
| 15 | 20 | 3.8% | 66% | 0% | 94% | 100% |

TABLE 5

The results reported in Table 5 were obtained at 80° C.

| Exp. | Time in min | DC mTFMA | YD N-allyl | YD di-allyl | Ac-counted for | Selectivity mono mono + di |
|---|---|---|---|---|---|---|
| 16 | 240 | 80.5% | 79% | 14.5% | 95% | 84.5% |
| 17 | 120 | 80.2% | 80.3% | 13.7% | 95% | 85.3% |
| 18 | 60 | 72% | 75.4% | 10.8% | 90% | 87.4% |
| 19 | 30 | 57% | 79% | 9% | 93.5% | 89.7% |
| 20 | 20 | 26% | 70% | 5% | 93.5% | 93.3% |

TABLE 6

The results reported in Table 6 were obtained at 90° C.

| Exp. | Time in min | DC mTFMA | YD N-allyl | YD di-allyl | Ac-counted for | Selectivity mono mono + di |
|---|---|---|---|---|---|---|
| 21 | 240 | 87.5 | 73.2% | 17.6% | 92% | 80.6% |
| 22 | 120 | 76.2% | 79.7% | 13.6% | 95% | 85.4% |
| 23 | 60 | 77% | 83.7% | 13.4% | 97.8% | 86.2% |
| 24 | 30 | 73% | 77% | 12.4% | 93% | 86.8% |
| 25 | 20 | 37% | 93.7% | 9.4% | 101% | 90.8% |

EXAMPLES 26 TO 29

ALLYLATION WITH ALLYL IODIDE

The procedure is as in Example 1, charging:
0.64 g of m-trifluoromethylaniline (4 mmol)
4 mmol of allyl iodide
2 ml of heptane
0.51 go of diisopropylethylamine (4 mmol)
and, where appropriate, 0.4 mmol of allyltriethylammonium bromide.

TABLE 7

The results of the process in Table 7 were obtained at 80° C. for four hours.

| Exp. | Allyl. agent | Ammonium | DC mTFMA | YD N-allyl | YD diallyl | Selectivity |
|---|---|---|---|---|---|---|
| 26 | I⌇⌇⌇ | no | 91.3% | 73.7% | 23.3% | 76% |
| 27 | I⌇⌇⌇ | yes | 89.5% | 79.4% | 17.6% | 81.8% |

TABLE 8

The results of the process in Table 8 were obtained at 80° C. for 2 hours 30 minutes.

| Exp. | Allyl. agent | Ammonium | DC mTFMA | YD N-allyl | YD diallyl | Selectivity |
|---|---|---|---|---|---|---|
| 28 | I⌇⌇⌇ | no | 76.7% | 76.8% | 13% | 85.5% |
| 29 | I⌇⌇⌇ | yes | 84.5% | 76.6% | 16% | 82,5% |

Other embodiments of the invention will be apparent to one skilled in the art from a consideration of the specification, or with the practice of the disclosed invention

We claim:

1. Process for the N-monoalkylation or N-monoallylation of an aniline, comprising the step of bringing the aniline and an alkylating or allylating agent, selected from the group consisting of alkyl chlorides, alkyl bromides, alkyl sulfates, allyl chlorides, allyl bromides and allyl sulfates, into contact in an organic solvent in a homogeneous liquid phase in the presence of an alkali metal iodide or onium iodide and a stoichiometric amount of a non-quarternizable base.

2. The process according to claim 1 wherein the allylating agent is allyl chloride.

3. The process according to claim 1 wherein the said aniline possesses a pKa of less than 4.5.

4. The process according to claim 3, wherein the aniline is chosen from the haloanilines, the perhaloalkylanilines, the perhaloalkoxyanilines, the perhaloalkylthioanilines and the nitroanilines of the formula (I)

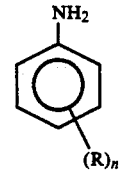

in which
R denotes:
  a halogen;
  a group $-AC_nX_{2n+1}$, where X denotes halogen and A denotes a covalent or an oxygen or sulfur atom;
  an $NO_2$ group;
n is equal to 1 or 2.

5. The process according to claim 1 wherein the said iodide is chosen from ammonium iodides and alkali metal iodides.

6. The process according to claim 5 wherein the onium compound is chosen from the ammoniums having a molecular weight of between 150 and 400.

7. The process according to claim 6 wherein the onium compound is a supported onium compound.

8. The process according to claim 1 wherein the said nonquaternizable base is an inorganic or organic base.

9. The process according to claim 8 wherein the non-quaternizable base is an organic base chosen from sodium acetate or a tertiary amine having at least one branched alkyl group.

10. The process according to claim 9 wherein the base is chosen from diisopropylallylamine, diisopropylethylamine and triisopropylamine.

11. The process according to claim 10 wherein the base is diisopropylethylamine.

12. The process according to claim 1 wherein the molar ratio of the aniline to the alkylating or allylating agent is approximately 1:1.

13. The process according to claim 1 wherein the molar ratio of the onium compound to the aniline is between 0.025 and 0.2.

14. The process according to claim 1 wherein the said organic solvent is chosen from aromatic or aliphatic hydrocarbon solvents, alcohols, aprotic polar solvents and non-quaternizable tertiary amines.

15. The process according to claim 14 wherein the chosen solvent is heptane or diisopropylethylamine.

16. The process as claimed in claim 1, wherein the alkylating agent is alkyl chloride.

17. The process according to claim 6, wherein the onium compound is chosen from the ammoniums having a molecular weight of between 200 and 300.

18. The process according to claim 9, wherein said tertiary amine has at least two branched alkyl groups.

* * * * *